United States Patent [19]
Taylor et al.

[11] Patent Number: 5,961,515
[45] Date of Patent: Oct. 5, 1999

[54] EXTERNAL SKELETAL FIXATION SYSTEM

[75] Inventors: Harold S. Taylor; J. Charles Taylor, both of Memphis, Tenn.

[73] Assignee: Smith & Nephew, Inc., Memphis, Tenn.

[21] Appl. No.: 08/396,512

[22] Filed: Mar. 1, 1995

[51] Int. Cl.[6] .................................................. A61B 17/66
[52] U.S. Cl. ............................................................ 606/59
[58] Field of Search ................................. 606/54, 55, 56, 606/57, 58, 59, 60, 72, 73

[56] References Cited

U.S. PATENT DOCUMENTS

| | | |
|---|---|---|
| 2,250,417 | 7/1941 | Ettinger . |
| 2,391,537 | 12/1945 | Anderson . |
| 3,941,123 | 3/1976 | Volkov et al. . |
| 4,033,340 | 7/1977 | Kalnberz . |
| 4,100,919 | 7/1978 | Oganesyan et al. . |
| 4,361,144 | 11/1982 | Slätis et al. . |
| 4,483,334 | 11/1984 | Murray . |
| 4,541,422 | 9/1985 | de Zbikowski . |
| 4,615,338 | 10/1986 | Ilizarov et al. . |
| 4,620,533 | 11/1986 | Mears . |
| 4,662,365 | 5/1987 | Gotzen et al. . |
| 4,889,111 | 12/1989 | Ben-Dov . |
| 4,978,348 | 12/1990 | Ilizarov ..................................... 606/57 |
| 5,062,844 | 11/1991 | Jamison et al. . |
| 5,160,335 | 11/1992 | Wagenknecht ............................ 606/59 |
| 5,209,750 | 5/1993 | Stef . |
| 5,261,909 | 11/1993 | Sutterlin et al. ........................... 606/61 |

FOREIGN PATENT DOCUMENTS

| | | |
|---|---|---|
| 1519673 A1 | 11/1989 | U.S.S.R. . |
| 2 077 847 | 12/1981 | United Kingdom . |
| WO94/23660 | 10/1994 | WIPO ...................................... 606/61 |

OTHER PUBLICATIONS

Richards Medical Company, *Richards External Fixation Systems*, 1983, 8 pages. Author unknown.

Richards Medical Company, *The Ilizarov External Fixator General Technique Brochure*, 1988, cover and p. 17. Author unknown.

Aspen Publishers, "Basic Ilizarov Techniques," *Techniques in Orthopaedics®*, vol. 5, No. 4, Dec. 1990, cover and pp. 57–58. Author unknown.

Pfizer Hospital Products Group, Inc. (Howmedica), *Monticelli Spinelli® External Fixation System*, 1991, cover and pp. 1–28.

*Hex–Fix Surgical Technique* brochure, title page and pp. 1–7. Date and Author unknown.

*Primary Examiner*—Michael Buiz
*Assistant Examiner*—David O. Reip
*Attorney, Agent, or Firm*—Pretty, Schroeder & Poplawski

[57] ABSTRACT

A pin-to-bar construct for an external fixation system of the type including a plurality of pins for securing first and second elements, and an elongated bar. The pin-to-bar construct includes a spool component for attachment to the bar; and an intermediate component for fixed attachment to the spool component and for joining at least one of the pins to the spool component. The intermediate component includes pin receiving structure for receiving one of the pins and intermediate component attachment structure for allowing fixed attachment to another intermediate component.

11 Claims, 6 Drawing Sheets

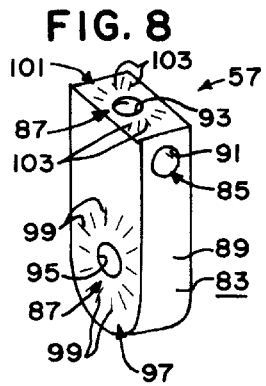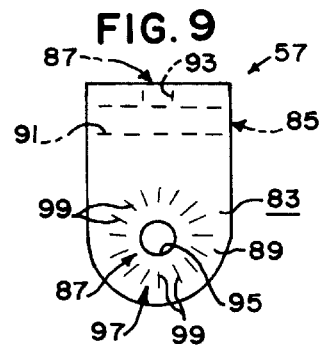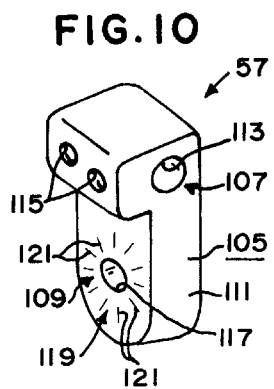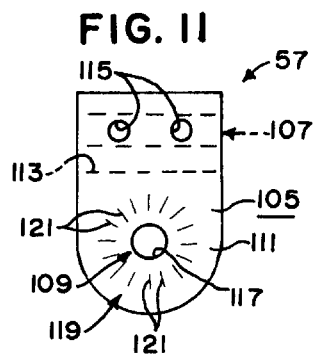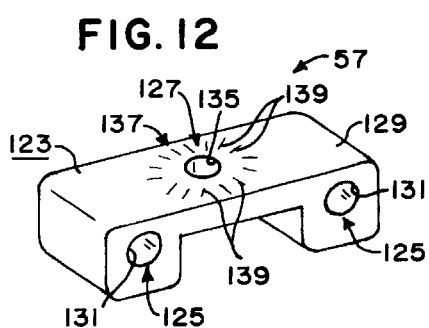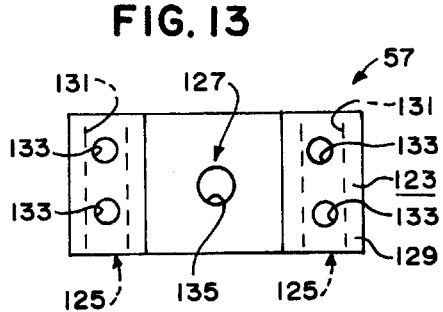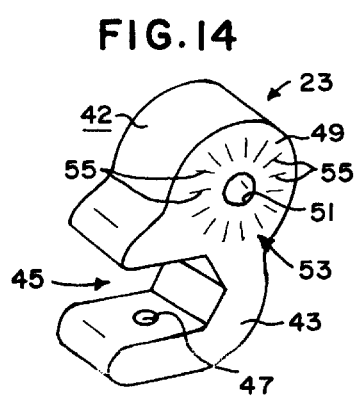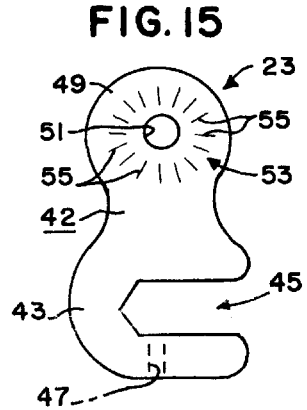

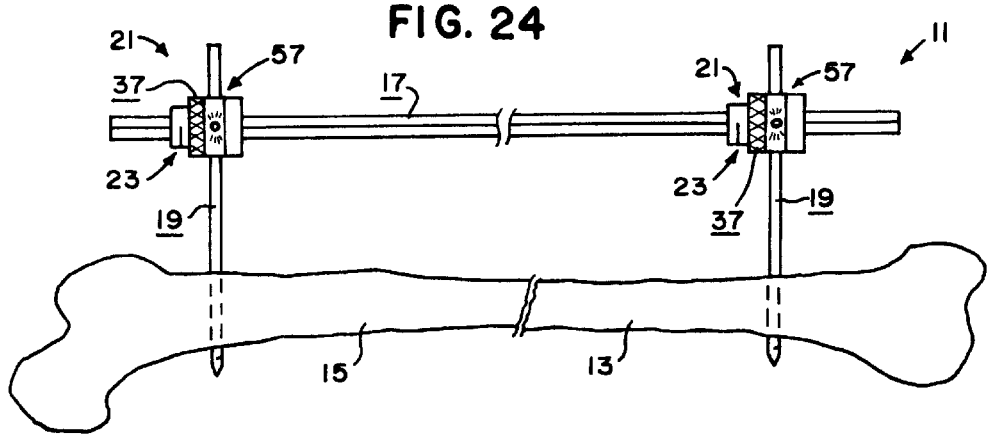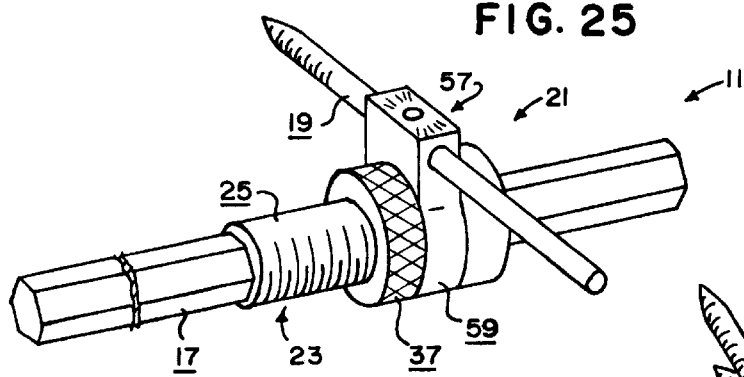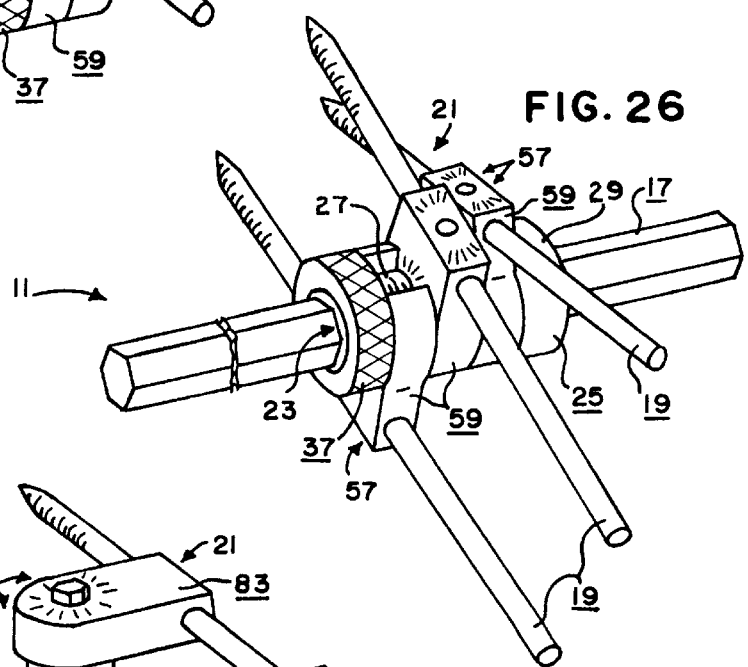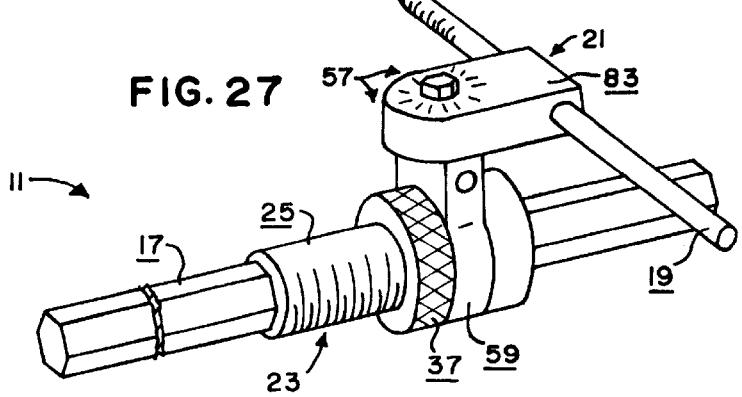

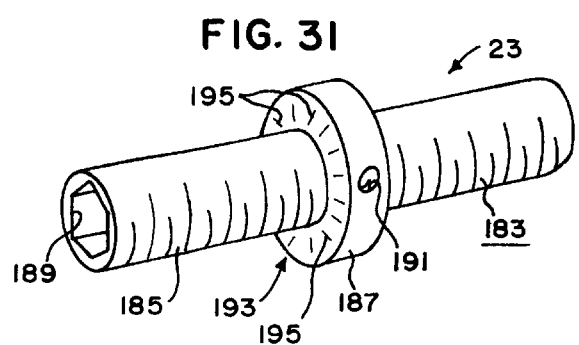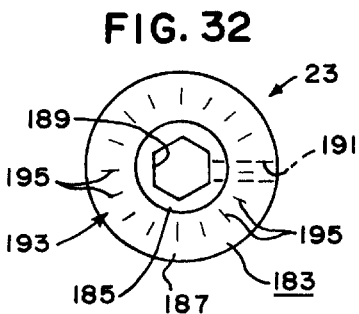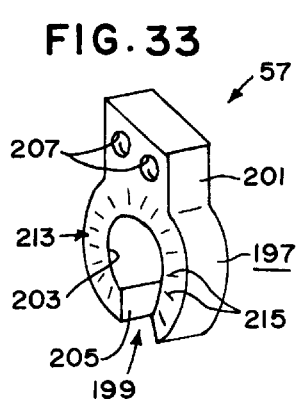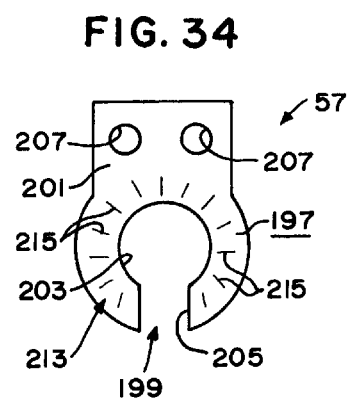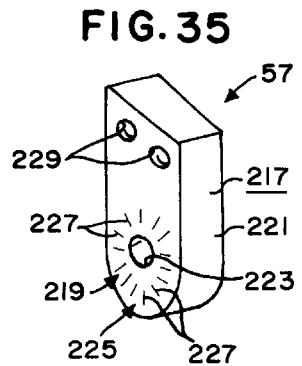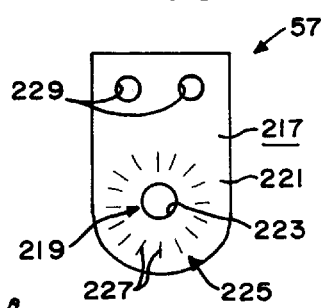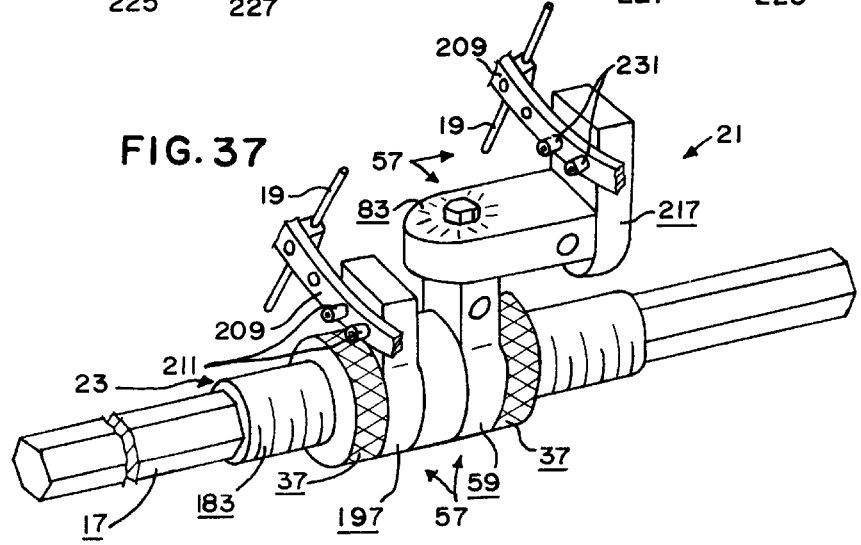

EXTERNAL SKELETAL FIXATION SYSTEM

BACKGROUND OF THE INVENTION

1. Field of the Invention

The present invention relates, in general, to a system for the external fixation of a boney skeleton and, more specifically, to a positive locking, orthogonally adjustable external fixation system which allows a plurality of components to be connected at each adjustment node.

2. Background Art

In the practice of medicine, it is sometimes desirable to treat certain injuries or conditions with a system including an external frame that is attached to the boney skeleton with threaded and/or smooth pins and/or threaded and/or smooth and/or beaded wires. Such systems are commonly referred to as orthopedic external fixators or external skeletal fixators. These external fixators may be utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting, etc.

External fixator frames vary considerably in design and capabilities, and may include multiple or single bars or rods, a plurality of pins or wires joined to the boney skeleton, and a plurality of clamps or connectors for adjustably securing the pins or wires to the bars or rods. The pins or wires may extend completely through the boney skeleton and out each side of the limb or may extend through the boney skeleton and out only one side of the limb. Pins which extend completely through the boney skeleton and out both sides of the limb are commonly referred to as "transfixation pins." Pins which extend through the boney skeleton and out only one side of the limb are commonly referred to as "half pins." Materials for frames also vary, including metals, alloys, plastics, composites, and ceramics. External fixators vary in their ability to accommodate different spatial relations between each pin and bar, etc.

External fixation is commonly used for fractures. Fractures which involve more than two major fragments are referred to as segmental fractures. Some external fixation systems with adjustment means primarily confined to either end of the external fixator cannot treat intermediate or intercalary fragments with the same adjustability as either terminal fragment. Such external fixation systems may include outrigger type pin clamps used to secure intermediate fragments without the same adjustability as given the terminal fragments. Malreduction of fracture fragments can require additional surgery to reposition, or if left uncorrected can lead to delayed or nonunion or to malunion with impaired or symptomatic function.

External skeletal fixation is accomplished by secure coupling of two or more pins or wires to each major bone fragment and attachment of these same pins or wires to a supporting frame. The exact location and orientation of these wires and pins are determined by the physician considering anatomic and mechanical factors. To accommodate the sometimes varied position and orientation of these pins and wires, external fixation systems have a variety of adjustment means with varying degrees of adjustability and versatility. Adjustment means of some systems use ball joints which permit unrestrained rotation in three planes but make adjustment in a single degree of freedom difficult since loosening the ball joint clamp to improve one rotation permits loss of position of formerly correctly reduced rotations. Additionally, ball joints depending only on stiction friction are prone to slippage with subsequent loss of position. In fact, it has been recommended that such ball joints be filled with a glue which when set would prevent slippage and loss of position. Other adjustment means include a cylinder pair which when loosened allow two simultaneous motions, translation and rotation. Again, individual adjustment is difficult or impossible and most cylinder pairs rely on stiction friction. In these cylinder pairs, the holding power of the clamp will also be a function of the coefficient of friction of the two parts.

Adjustment means utilizing mechanically constrained surfaces such as radial splined faces provide positive locking of parts. Holding power relies more on geometry of mating parts and shear strength of constituent materials. Different systems incorporate mechanically constrained clamping mechanisms to different extents, including stiction friction ball joints, radial face splines on two of three rotations with the remaining rotation controlled by a stiction friction cylinder pair in combination with a translation, and three independent adjustments utilizing mating radial splined faces. Such adjustment means provide for independent adjustment of different rotations and also positive locking by virtue of mechanically constrained couplings.

In the course of treatment with external fixation, it is sometimes desirable or preferable to translate one or more bone fragments or to lengthen bones along an axis parallel to the axis of an external fixator bar. During such controlled translation or movement, it is desirable to maintain or control the other spatial relations of each fragment.

Ettinger, U.S. Pat. No. 2,250,417, issued Jul. 22, 1941, discloses an orthopedic external fixator for fracture reduction and retention including an elongated bar, a plurality of elongated threaded pins for transfixing bone elements, a first connector or head attached to one end of the bar for joining a pair of the pins to the bar, and a second connector or sleeve slidably positioned on the bar for connecting another pair of the pins to the bar. A portion of the bar is externally threaded and two nuts are screwably mounted on the bar, one on either end of the sleeve, so that proper rotation of the nuts will cause the sleeve and associated pins to move along the bar. The bar has either a circular cross section with a longitudinal keyway for receiving a key of the sleeve, or a square cross section with rounded, threaded corners in which case the sleeve is provided with a square bore to hold the sleeve against rotation on the bar.

Anderson, U.S. Pat. No. 2,391,537, issued Dec. 25, 1945, discloses an orthopedic external fixator for fracture reduction including a pair of hollow tubes telescopically joined together, a plurality of pins for transfixing bone elements, a first fixation unit slidably mounted on the first tube for connecting a pair of the transfixion pins to the first tube, and a second fixation unit attached to the end of the second tube for connecting a pair of the transfixation pins to the second tube. The second tube is telescopically mounted within the first tube. A threaded adjusting shaft is mounted within the tubes and can be manually rotated by way of a wrench head located at the outer end of the second tube. Rotation of the shaft causes a nut nonrotatably located within the second tube to move longitudinally along the shaft. Coil springs located within the tubes on either side of the nut transfer longitudinal movement of the nut to the tubes while permitting a certain desired yielding and eliminating any perfectly solid and hard contact.

Mears, U.S. Pat. No. 4,620,533, issued Nov. 4, 1986, discloses an orthopedic external fixator including a plurality of transfixation pins, an elongated bar, and a plurality of pin-to-bar clamps for adjustably attaching the pins to the bar. The pin-to-bar clamps including articulating balls for holding the pins and the bar when thumbscrews or the like are tightened. In addition, Mears discloses a bar-to-bar clamp for allowing a first elongated bar to be clamped relative to a second elongated bar.

Gotzen et al., U.S. Pat. No. 4,662,365, issued May 5, 1987, discloses a device for the external fixation of bone fragments including an elongated supporting bar, a plurality of bone pins, and a plurality of clamp assemblies for attaching the pins to the bar.

Nothing in the known prior art discloses or suggests the present invention. More specifically, nothing in the known prior art discloses or suggests a skeletal fixation system including a spool component for attachment to a bar; and an intermediate component for fixed attachment to the spool component and for joining at least one pin to the spool component, the intermediate component including pin receiving means for receiving one pin and intermediate component attachment means for allowing fixed attachment to another intermediate component.

SUMMARY OF THE INVENTION

The present invention provides an external skeletal fixation system which allows segmental fixation of one or more fragments. Unique components allow individual pins and pairs of pins to be rotated in three orthogonal planes and positively locked using splined faces on components. Novel component shapes and the use of coupling bolts rather than threaded posts permits multiple components to be used at each component junction or node between two or more components. Furthermore, these components are held securely by the positive locking of opposed radial splined faces. The system permits the 'transfer' of pins from one segment of fixation to an adjacent fixation segment without the need to remove skeletal fixation pins.

The skeletal fixation system of the present invention comprises, in general, a spool component for attachment to a bar; and an intermediate component for fixed attachment to the spool component and for joining at least one pin to the spool component, the intermediate component including pin receiving means for receiving one pin and intermediate component attachment means for allowing fixed attachment to another intermediate component.

One object of the present invention is to provide a skeletal fixation system that allows different classes of components to be used together and used multiply.

Another object of the present invention is to provide a system that allows segmental fixation for stabilizing several major fragments each with adjustability; that utilizes mechanically constrained adjustment surfaces; that allows independent adjustability of each orthogonal rotation; that allows multiple components to be positively joined at each component junction or node; that allows different classes of intermediate components to be positively joined at each component junction or node; and that allows partial disassembly or modification to be able to transfer pins from one intermediate component to another and/or attach accessories without having to remove pins from bone.

Another object of the present invention is to provide a system that allows multiple components to be joined at each component junction or node.

Another object of the present invention is to provide a system that allows the coupling of different classes of intermediate components (e.g. pin clamps and intermediate paddles coupled to an intermediate paddle) at each component junction.

Another object of the present invention is to provide a system that provides positive locking splines at each mating surface.

Another object of the present invention is to provide a system that allows the transfer of pins from one pin clamp to a nearby pin clamp without requiring the removal and reinsertion of the pin.

Another object of the present invention is to provide a system that allows multiple pin clamps and or intermediate components to be attached to a translating spool.

Another object of the present invention is to provide a system that allows attachment of multiple intermediate components or pin clamps.

BRIEF DESCRIPTION OF THE DRAWINGS

FIG. 8 is a perspective view of an intermediate paddle of the external fixation system of the present invention, taken generally from the left end.

FIG. 9 is a right end elevational view of the intermediate paddle of FIG. 8.

FIG. 10 is a perspective view of a terminal single pin clamp of the external fixation system of the present invention, taken generally from the left end.

FIG. 11 is a right end elevational view of the terminal single pin clamp of FIG. 10.

FIG. 12 is a perspective view of a terminal double pin clamp of the external fixation system of the present invention, taken generally from the top.

FIG. 13 is a bottom plan view of the terminal double pin clamp of FIG. 12.

FIG. 14 is a perspective view of an open throat spool of the external fixation system of the present invention, taken generally from the right side.

FIG. 15 is a left side elevational view of the open throat spool clamp of FIG. 14.

FIG. 24 is a diagrammatic elevation view of the external fixation system of the present invention in combination with a fractured femur.

FIG. 25 is a perspective view of a portion of the external fixation system of the present invention, showing a first embodiment of the bar-to-pin construct thereof.

FIG. 26 is a perspective view of a portion of the external fixation system of the present invention, showing a second embodiment of the bar-to-pin construct thereof.

FIG. 27 is a perspective view of a portion of the external fixation system of the present invention, showing a third embodiment of the bar-to-pin construct thereof.

FIG. 31 is a perspective view of a double spool of the external fixation system of the present invention, taken generally from the left end.

FIG. 32 is a right end elevational view of the double spool of FIG. 31.

FIG. 33 is a perspective view of an open throat ring adapter paddle of the external fixation system of the present invention, taken generally from the left side.

FIG. 34 is a right end elevational view of the open throat ring adapter paddle of FIG. 33.

FIG. 35 is a perspective view of an intermediate ring adapter paddle of the external fixation system of the present invention, taken generally from the left side.

FIG. 36 is a right end elevational view of the intermediate ring adapter paddle of FIG. 35.

FIG. 37 is a perspective view of a portion of the external fixation system of the present invention, showing a seventh embodiment of the bar-to-pin construct thereof.

DESCRIPTION OF THE PREFERRED EMBODIMENT

Figure 1:
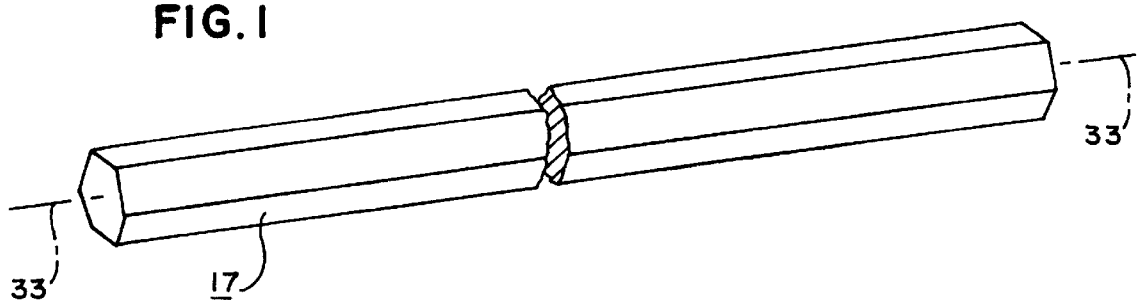
FIG. 1 is a perspective view of an external fixation rod of the external fixation system of the present invention, taken generally from the left end and with portions thereof broken away for clarity.

Various preferred embodiments of the external fixation system of the present invention are shown in FIGS. 24–30, and identified by the numeral 11. The external fixation system 11 is used to secure one or more elements. For example, as diagrammatically shown in FIG. 24, the external fixation system 11 can be used as an external skeletal fixation system to secure or fix a first bone element 13 relative to a second bone element 15, etc., in the event of a break, fracture, etc.

As shown generally in FIGS. 24–30 and 37, the external fixation system 11 includes an elongated shaft, tube or bar 17; a plurality of pins 19 for being inserted into and securing the first and second bone elements 13, 15; and a plurality of pin-to-bar constructs 21 for joining the pins 19 to the bar 17. The word "pin" is used herein to encompass standard transfixation pins, half pins, wires, and the like.

The bar 17 may consist of a rigid, elongated metal member as will now be apparent to those skilled in the art, such as, for example, the supporting bar 2 disclosed in Gotzen et al., U.S. Pat. No. 4,662,365, issued May 5, 1987, incorporated herein by reference. Preferably, the bar 17 has a non-revolute cross-sectional shape for reasons which will hereinafter become apparent. Representative non-revolute cross-sectional shapes of the bar 17 include but are not limited to regular and irregular triangles, rectangles, pentagons, hexagons, septagons, octagons, nonagons, decagons, etc. Other possible cross-sectional shapes include keyed circular cross-sectional shapes and curved cross-sectional shapes other than circular, such as, for example, elliptical. As clearly shown in FIG. 1, the bar 17 preferably has a hexagonal cross-sectional shape.

The pins 19 may consist of a threaded and/or smooth pin or screw and/or a threaded and/or smooth and/or beaded wire as typically used in the external fixation of bone fractures for securing the boney skeleton to an external frame or the like as will now be apparent to those skilled in the art, such as, for example, the bone pins 3 discloses in Gotzen et al., U.S. Pat. No. 4,662,365, issued May 5, 1987, incorporated herein by reference.

The pin-to-bar constructs 21 can be assembled from a number of different individual components to form a number of different embodiments thereof as shown generally in FIGS. 25–29, depending on specific circumstances and in a manner which allows segmental fixation of one or more fracture, etc., as will hereinafter become apparent.

Each pin-to-bar construct 21 includes a spool component 23 for attachment to the bar 17.

Figure 2:
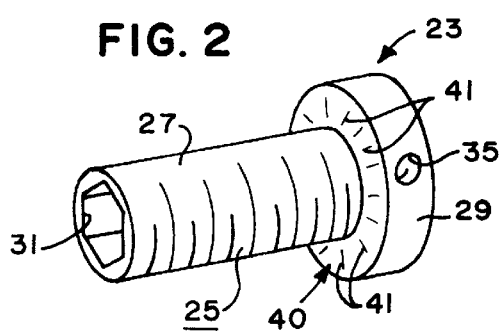
FIG. 2 is a perspective view of a spool of the external fixation system of the present invention, taken generally from the left end.
Figure 3:
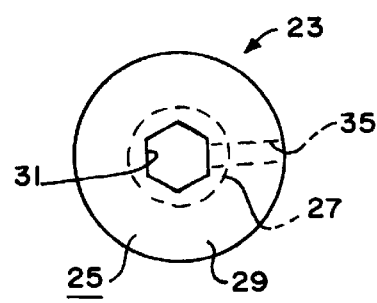
FIG. 3 is a right end elevational view of the spool of FIG. 2.
Figure 6:
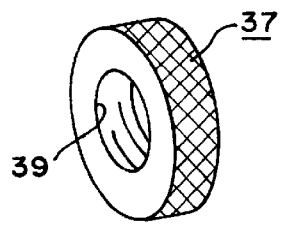
FIG. 6 is a perspective view of a locking ring of the external fixation system of the present invention, taken generally from the left end.
Figure 7:
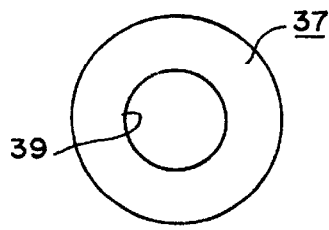
FIG. 7 is a right end elevational view of the locking ring of FIG. 6.

One embodiment of the spool component 23 is shown in FIGS. 2 and 3, and consist of a single spool 25 including a cylindrical body 27 and a flange 29 at one end of the body 27. The body 27 has a longitudinal aperture or bore 31 extending therethrough for slidably receiving the bar 17. The bore 31 may have a nonrevolute cross-sectional shape for non-rotatably mating with the nonrevolute cross section of the bar 17. Thus, the cross-sectional shape of the bore 31 is complementary with the cross section of the bar 17 so that rotation (within tolerances) of the spool 25 around the longitudinal axis 33 of the bar 17 is prevented. As shown in FIGS. 2 and 3, the bore 31 preferably has a hexagonal cross-sectional shape corresponding to and complementary with the hexagonal cross-sectional shape of the bar 17. A threaded aperture 35 preferably extends through the flange 29 transverse to the longitudinal axis of the bore 31 for allowing a set screw or the like (not shown) to be used to fixedly secure the spool 25 to the bar 17 as will now be apparent to those skilled in the art. The external surface of the body 27 is preferably threaded for screwably receiving a locking ring 37 as will hereinafter become apparent. The locking ring 37 has an internally threaded aperture 39 as shown in FIGS. 6 and 7 for screwably coacting with the externally threaded body 27 of the spool 25. Additionally, the locking ring 37 preferably has a knurled exterior for allowing it to be easily manually turned as will hereinafter become apparent. Grip enhancing means 40 is preferably provided on the side of the flange 29 adjacent the body 27 for reasons which will hereinafter become apparent. The grip enhancing means 40 preferably consist of a plurality of raised or indented splines or teeth 41 formed in the surface of the flange 29 and radiating from the center of the bore 31.

Another embodiment of the spool component 23 is shown in FIGS. 14 and 15, and consist of an open throat spool 42 including a plate-like body 43 having an open throat or slot 45 for slidably receiving the bar 17. The slot 45 may have a nonrevolute cross-sectional shape for non-rotatably mating with the nonrevolute cross section of the bar 17. Thus, the cross-sectional shape of at least a portion of the slot 45 is complementary with the cross section of at least a portion of the bar 17 so that rotation (within tolerances) of the spool 42 around the longitudinal axis 33 of the bar 17 is prevented. As shown in FIGS. 14 and 15, the closed end of the slot 45 preferably has a partial hexagonal cross-sectional shape corresponding to and complementary with the hexagonal cross-sectional shape of the bar 17. A threaded aperture 47 preferably extends through the body 43 into the slot 45 for allowing a set screw or the like (not shown) to be used to fixedly secure the spool 42 to the bar 17 as will now be apparent to those skilled in the art. The spool 42 preferably has an ear 49 attached to the body 43 for allowing various intermediate components to be coupled thereto. The ear 49 preferably has an aperture 51 therethrough. Grip enhancing means 53 are preferably provided on both sides of the ear 49 adjacent the mouth or open ends of the aperture 51 for reasons which will hereinafter become apparent. The grip enhancing means 53 preferably consist of a plurality of raised or indented splines or teeth 55 formed in the ear 49 and radiating from the center of the aperture 51.

Each pin-to-bar construct 21 includes a intermediate component 57 for joining at least one of the pins 19 to a spool component 23.

Figure 4:
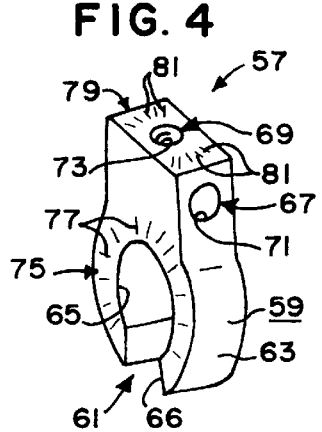
FIG. 4 is a perspective view of a spool paddle of the external fixation system of the present invention, taken generally from the left end.
Figure 5:
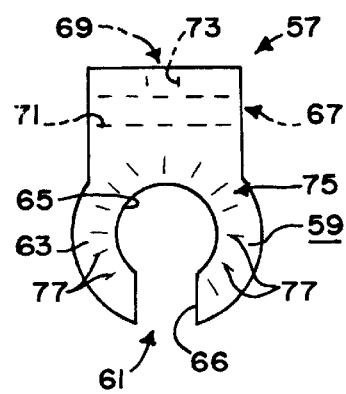
FIG. 5 is a right end elevational view of the spool paddle of FIG. 4.

One embodiment of the intermediate component 57 is shown in FIGS. 4 and 5, and consist of a spool paddle 59 including spool component attachment means 61 for allowing fixed attachment to the spool component 23. For example, the spool paddle 59 may include a body 63 having an aperture 65 therethrough for passing over the body 27 of the spool 25 and for forming or defining the spool component attachment means 61. The aperture 65 may have an open slot or mouth 66 for allowing the spool paddle 59 to be inserted over the bar 17 and onto the body 27 of the spool 25 intermediate the opposite ends thereof. Without the open slot or mouth 66, the spool paddle 59 will have to be slipped over the distal ends of both the bar 17 and the body 27 of the spool 25. The spool paddle 59 includes pin receiving means 67 for receiving one of the pins 19, and intermediate component attachment means 69 for allowing direct contact fixed attachment to another intermediate component 57. More specifically, the body 63 may have an aperture or bore 71 extending thereacross for slidably receiving the shank, etc., of one of the pins 19 and for forming or defining the pin receiving means 67. Further, the body 63 may have an internally threaded aperture 73 opening into the bore 71 for coacting with a screw or bolt to secure one or more other intermediate components 57 to the body 63 to thereby form or define the intermediate component attachment means 69, and/or to secure a pin 19 within the bore 71. Grip enhancing means 75 are preferably provided on both sides of the body 63 adjacent both open ends of the aperture 65 for reasons which will hereinafter become apparent. The grip enhancing means 75 preferably consist of a plurality of raised or indented splines or teeth 77 formed in the body 63 and radiating from the center of the aperture 65. Grip enhancing means 79 is preferably provided on the body 63 adjacent the mouth or open end of the threaded aperture 73 for reasons which will hereinafter become apparent. The grip enhancing means 79 preferably consist of a plurality of raised or indented splines or teeth 81 formed in the body 63 and radiating from the center of the threaded aperture 73.

Another embodiment of the intermediate component 57 is shown in FIGS. 8 and 9 and consist of an intermediate paddle 83 including pin receiving means 85 for receiving one of the pins 19, and a pair of intermediate component attachment means 87 for allowing direct contact fixed attachment to one, two or three other intermediate component 57. For example, the intermediate paddle 83 may include a body 89 having an aperture or bore 91 extending thereacross for slidably receiving the shank, etc., of one of the pins 19 and for forming or defining the pin receiving means 85. Further, the body 89 may have an internally threaded aperture 93 opening into the bore 91 for coacting with a screw or bolt to secure one or more other intermediate components 57 to the body 89 to thereby form or define one intermediate component attachment means 87, and/or to secure a pin 19 within the bore 91. In addition, the body 89 may have another aperture or bore 95 extending thereacross for coacting with a screw or bolt to secure one or more other intermediate components 57 to the body 89 to thereby form or define another intermediate component attachment means 87. Grip enhancing means 97 are preferably provided on both sides of the body 89 adjacent both open ends of the bore 95 for reasons which will hereinafter become apparent. The grip enhancing means 97 preferably consist of a plurality of raised or indented splines or teeth 99 formed in the body 89 and radiating from the center of the bore 95. Grip enhancing means 101 is preferably provided on the body 89 adjacent the mouth or open end of the threaded aperture 93 for reasons which will hereinafter become apparent. The grip enhancing means 101 preferably consist of a plurality of raised or indented splines or teeth 103 formed in the body 89 and radiating from the center of the threaded aperture 93.

Another embodiment of the intermediate component 57 is shown in FIGS. 10 and 11 and consist of terminal single pin clamp 105 including pin receiving means 107 for receiving one of the pins 19, and intermediate component attachment means 109 for allowing direct contact fixed attachment to another intermediate component 57. For example, the terminal single pin clamp 105 may include a body 111 having an aperture or bore 113 extending thereacross for slidably receiving the shank, etc., of one of the pins 19 and for forming or defining the pin receiving means 107. Further, the body 111 may have a pair of internally threaded apertures 115 opening into the bore 113 for coacting with set screws or the like to secure a pin 19 within the bore 113. In addition, the body 111 may have an aperture or bore 117 extending thereacross for coacting with a screw or bolt to secure one or more other intermediate components 57 to the body 111 to thereby form or define the intermediate component attachment means 109. Grip enhancing means 119 are preferably provided on both sides of the body 111 adjacent both open ends of the bore 117 for reasons which will hereinafter become apparent. The grip enhancing means 119 preferably consist of a plurality of raised or indented splines or teeth 121 formed in the body 111 and radiating from the center of the bore 117.

Another embodiment of the intermediate component 57 is shown in FIGS. 12 and 13 and consist of terminal double pin clamp 123 including a pair of pin receiving means 125 for receiving one or more pins 19, and intermediate component attachment means 127 for allowing direct contact fixed attachment to another intermediate component 57. For example, the terminal double pin clamp 123 may include a body 129 having a pair of spaced apart apertures or bores 131 extending thereacross for slidably receiving the shank, etc., of one or more pins 19 with each bore 131 forming or defining a pin receiving means 125. Further, the body 129 may have a pair of internally threaded apertures 133 opening into each bore 131 for coacting with set screws or the like to secure a pin 19 within each bore 131. In addition, the body 129 may have an aperture or bore 135 extending thereacross for coacting with a screw or bolt to secure one or more other intermediate components 57 to the body 129 to thereby form or define the intermediate component attachment means 127. Grip enhancing means 137 are preferably provided on one side of the body 129 adjacent one open end of the bore 135 for reasons which will hereinafter become apparent. The grip enhancing means 137 preferably consist of a plurality of raised or indented splines or teeth 139 formed in the body 129 and radiating from the center of the bore 135.

Figure 21:
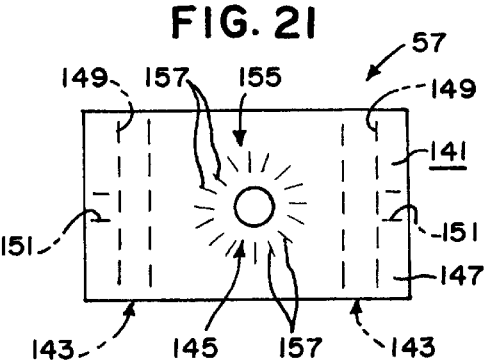
FIG. 21 is a top plan view of a double pin clamp of the external fixation system of the present invention.
Figure 22:
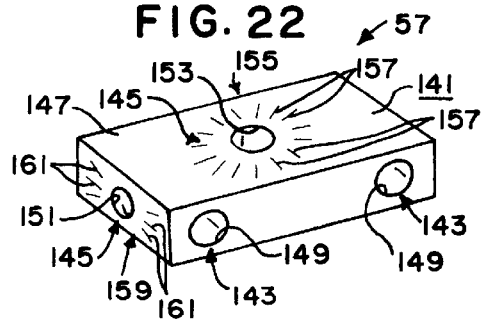
FIG. 22 is a perspective view of the double pin clamp of FIG. 21, taken generally from the left end.
Figure 23:
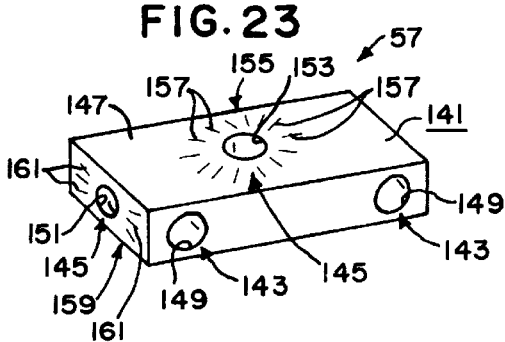
FIG. 23 is a perspective view of the double pin clamp of FIG. 21, taken generally from the right end.

Another embodiment of the intermediate component 57 is shown in FIGS. 21–23 and consist of double pin clamp 141 including a pair of pin receiving means 143 for receiving one or more pins 19, and intermediate component attachment means 145 for allowing direct contact fixed attachment to another intermediate component 57. For example, the double pin clamp 141 may include a body 147 having a pair of spaced apart apertures or bores 149 extending thereacross for slidably receiving the shank, etc., of one or more pins 19 with each bore 149 forming or defining a pin receiving means 143. Further, the body 147 may have an internally threaded aperture 151 opening into each bore 149 for coacting with a screw or bolt to secure one or more other intermediate components 57 to the body 147 to thereby form or define one intermediate component attachment means 145, and/or to secure a pin 19 within a bore 149. In addition, the body 147 may have another aperture or bore 153 extending thereacross for coacting with a screw or bolt to secure one or more other intermediate components 57 to the body 147 to thereby form or define another intermediate component attachment means 145. Grip enhancing means 155 are preferably provided on both sides of the body 147 adjacent both open ends of the bore 153 for reasons which will hereinafter become apparent. The grip enhancing means 155 preferably consist of a plurality of raised or indented splines or teeth 157 formed in the body 147 and radiating from the center of the bore 153. Grip enhancing means 159 are preferably provided on the body 147 adjacent the mouth or open end of each threaded aperture 151 for reasons which will hereinafter become apparent. The grip enhancing means 159 preferably consist of a plurality of raised or indented splines or teeth 161 formed in the body 147 and radiating from the center of each threaded aperture 151.

Figure 16:
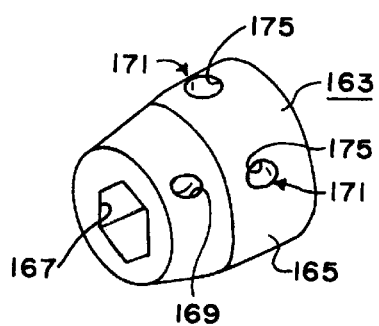
FIG. 16 is a perspective view of a terminal attachment spool of the external fixation system of the present invention, taken generally from the left end.
Figure 17:
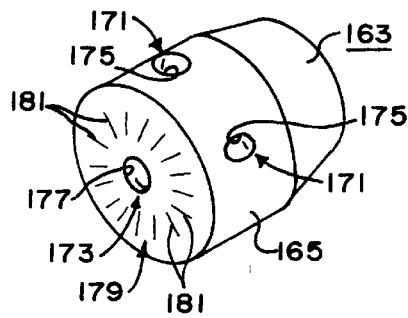
FIG. 17 is a perspective view of the terminal attachment spool of FIG. 16, taken generally from the right end.
Figure 18:
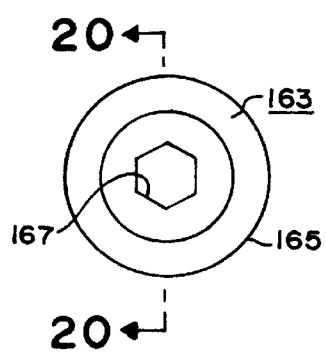
FIG. 18 is a left end elevational view of the terminal attachment spool of FIG. 16.
Figure 19:
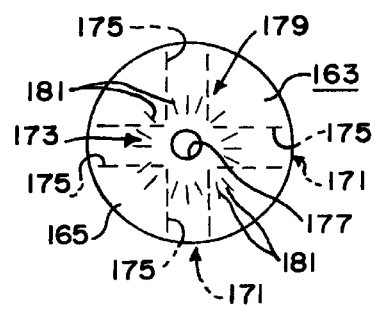
FIG. 19 is a right end elevational view of the terminal attachment spool of FIG. 16.
Figure 20:
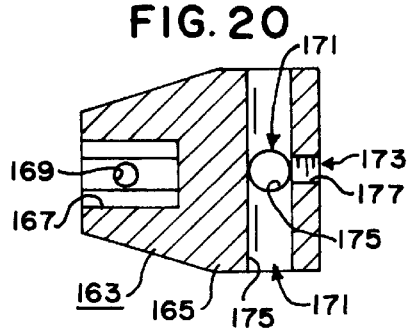
FIG. 20 is a sectional view substantially as taken on line 20-20 of FIG. 18.

FIGS. 16–20 show a combined, integral spool and intermediate component, consisting of a terminal attachment 163 including a body 165 having a longitudinal, closed-end aperture or bore 167 extending partially therethrough for receiving one end of the bar 17. The bore 167 may have a nonrevolute cross-sectional shape for nonrotatably mating with the nonrevolute cross section of the bar 17. Thus, the cross-sectional shape of the bore 167 is preferably complementary with the cross section of the bar 17 so that rotation (within tolerances) of the terminal attachment 163 around the longitudinal axis 33 of the bar 17 is prevented. As shown in FIGS. 16 and 18, the bore 167 preferably has a hexagonal cross-sectional shape corresponding to and complementary with the hexagonal cross-sectional shape of the bar 17. A threaded aperture 169 preferably extends through the body 165 substantially transverse to the longitudinal axis of the bore 167 for allowing a set screw or the like to be used to fixedly secure the terminal attachment 163 to the bar 17 as will now be apparent to those skilled in the art.

The terminal attachment 163 also includes pin receiving means 171 for receiving one of the pins 19, and intermediate component attachment means 173 for allowing direct contact fixed attachment to another intermediate component 57. More specifically, the body 165 may have a pair of apertures or bores 175 extending thereacross for slidably receiving the shank, etc., of one of the pins 19 and for forming or defining the pin receiving means 67. Further, the body 165 may have an internally threaded aperture 177 opening into the bores 175 for coacting with a screw or bolt to secure one or more other intermediate components 57 to the body 165 to thereby form or define the intermediate component attachment means 173, and/or to secure a pin 19 within one of the bores 175. Grip enhancing means 179 are preferably provided on the body 165 adjacent the open end of the aperture 177 for reasons which will hereinafter become apparent. The grip enhancing means 179 preferably consist of a plurality of raised or indented splines or teeth 181 formed in the body 165 and radiating from the center of the aperture 177.

Another embodiment of the spool component 23 is shown in FIGS. 31 and 32, and consist of a double spool 183 including a cylindrical body 185 and a flange 187 intermediate the opposite ends of the body 185. The body 187 has a longitudinal aperture or bore 189 extending therethrough for slidably receiving the bar 17. The bore 189 may have a nonrevolute cross-sectional shape for non-rotatably mating with the nonrevolute cross section of the bar 17. Thus, the cross-sectional shape of the bore 189 is complementary with the cross section of the bar 17 so that rotation (within tolerances) of the spool 183 around the longitudinal axis 33 of the bar 17 is prevented. As shown in FIGS. 31 and 32, the bore 189 preferably has a hexagonal cross-sectional shape corresponding to and complementary with the hexagonal cross-sectional shape of the bar 17. A threaded aperture 191 preferably extends through the flange 187 transverse to the longitudinal axis of the bore 189 for allowing a set screw or the like (not shown) to be used to fixedly secure the spool 183 to the bar 17 as will now be apparent to those skilled in the art. The external surface of the body 185 is preferably threaded for screwably receiving a locking ring 37 on one or both sides of the flange 187 as will hereinafter become apparent. Grip enhancing means 193 are preferably provided on both sides of the flange 187 for reasons which will hereinafter become apparent. The grip enhancing means 193 preferably consist of a plurality of raised or indented splines or teeth 195 formed in the surface of both sides of the flange 187 and radiating from the center of the bore 189.

Another embodiment of the intermediate component 57 is shown in FIGS. 33 and 34, and consist of a spool paddle 197 including spool component attachment means 199 for allowing fixed attachment to the spool component 23. For example, the spool paddle 197 may include a body 201 having an aperture 203 therethrough for passing over the body 27 of the spool 25 or the body 185 of the spool 183, and for forming or defining the spool component attachment means 199. The aperture 203 may have an open slot or mouth 205 for allowing the spool paddle 197 to be inserted over the body 27 of the spool 25 or the body 185 of the spool 183, intermediate the opposite ends thereof. Without the open slot or mouth 205, the spool paddle 197 will have to be slipped over the distal ends of both the bar 17 and the body 27 of the spool 25 or the body 185 of the spool 183. The spool paddle 197 may have one or more apertures 207 through the body 201 for allowing direct contact fixed attachment to a typical "halo" ring 209 (see FIG. 37) of any well know "Ilizarov-type" circumferential external fixator system. The apertures 207 may be threaded to allow standard bolts 211 (see FIG. 37) or the like to be used to secure the ring 209 to the spool paddle 197 as will now be apparent to those skilled in the art. Grip enhancing means 213 are preferably provided on both sides of the body 201 adjacent both open ends of the aperture 203 for reasons which will hereinafter become apparent. The grip enhancing means 213 preferably consist of a plurality of raised or indented splines or teeth 215 formed in the body 201 and radiating from the center of the aperture 203.

Another embodiment of the intermediate component 57 is shown in FIGS. 35 and 36 and consist of an intermediate ring adapter 217 including intermediate component attachment means 219 for allowing direct contact fixed attachment to another intermediate component 57. For example, the intermediate ring adapter 217 may include a body 221 having an aperture or bore 223 extending thereacross for coacting with a screw or bolt to secure one or more other intermediate components 57 to the body 221 to thereby form or define the intermediate component attachment means 219. Grip enhancing means 225 are preferably provided on both sides of the body 221 adjacent both open ends of the bore 223 for reasons which will hereinafter become apparent. The grip enhancing means 225 preferably consist of a plurality of raised or indented splines or teeth 227 formed in the body 221 and radiating from the center of the bore 223. The intermediate ring adapter 217 may also have one or more apertures 229 through the body 221 for allowing direct contact fixed attachment to a typical "halo" ring 209 (see FIG. 37) of any well know "Ilizarov-type" circumferential external fixator system. The apertures 229 may be threaded to allow standard bolts 231 (see FIG. 37) or the like to be used to secure the ring 209 to the intermediate ring adapter 217 as will now be apparent to those skilled in the art.

As thus constructed, the various components of the external fixation system 11 provide a versatile system that allows segmental fixation of one or more fragments, allows individual pins and pairs of pins to be rotated in three orthogonal planes and positively locked using splined faces on components, permits multiple components to be used at each component junction or node between two or more components, allows adjacent components to be positively locked to one another; and permits the 'transfer' of pins from one segment of fixation to an adjacent fixation segment without the need to remove skeletal fixation pins, etc. With reference to FIGS. 25–30, several of the various specific pin-to-bar constructs allowed by the present invention will now be described.

FIG. 25 shows a simple, one-pin construct in which a single spool 25 is attached to a bar 17, one spool paddle 59 is attached to the spool 25 by being clamped between the flange 29 of the single spool 25 and a locking ring 37, and a single pin 19 is attached to the spool paddle 59. The coaction between the grip enhancing means 40 on the flange 29 of the spool 25 and the grip enhancing means 75 on one side of the body 63 of the spool paddle 59 allows accurate and positive angular adjustment of the spool paddle 59 and pin 19 about the longitudinal axis 33 of the bar 17 as will now be apparent to those skilled in the art.

FIG. 26 shows a multiple-pin construct in which a single spool 25 is attached to a bar 17, a plurality of spool paddles 59 are attached to the spool 25 and stacked side-by-side by being clamped between the flange 29 of the single spool 25 and a locking ring 37, and a single pin 19 is attached to each spool paddle 59. The coaction between the grip enhancing means 40 on the flange 29 of the spool 25 and the grip enhancing means 75 on the sides of the bodies 63 of the spool paddles 59 allows accurate and positive angular adjustment of the spool paddles 59 and pins 19 about the longitudinal axis 33 of the bar 17 as will now be apparent to those skilled in the art. FIG. 26 also illustrates the unique feature of the present invention in which the body 27 of the spool 25 has a sufficient length to allow a first intermediate component 57 (e.g., a first spool paddle 59) to be placed on the body 27 of the spool 25 in abutting engagement with the flange 29, to allow a second intermediate component 57 (e.g., a second spool paddle 59) to be placed on the body 27 of the spool 25 in abutting engagement the first intermediate component 57 (e.g., the first spool paddle 59), to allow a third intermediate component 57 (e.g., a third spool paddle 59) to be placed on the body 27 of the spool 25 in abutting engagement the second intermediate component 57 (e.g., the second spool paddle 59), and to allow the locking component (e.g., the locking ring 37) to be placed on the body 27 of the spool 25 in abutting engagement with the third intermediate component (e.g., the third spool paddle 59).

FIG. 27 shows a simple, one-pin construct in which a single spool 25 is attached to a bar 17, one spool paddle 59 is attached to the spool 25 by being clamped between the flange 29 of the single spool 25 and a locking ring 37, one intermediate paddle 83 is attached to the spool paddle 59, and a single pin 19 is attached to the intermediate paddle 83. The coaction between the grip enhancing means 40 on the flange 29 of the spool 25 and the grip enhancing means 75 on one side of the body 63 of the spool paddle 59 allows accurate and positive angular adjustment of the spool paddle 59 and pin 19 about the longitudinal axis 33 of the bar 17 as will now be apparent to those skilled in the art. Likewise, the coaction between the grip enhancing means 79 on the body 63 of the spool paddle 59 and the grip enhancing means 97 on one side of the body 89 of the intermediate paddle 83 allows accurate and positive angular adjustment of the intermediate paddle 83 and pin 19 about an axis substantially transverse to the longitudinal axis 33 of the bar 17 as will now be apparent to those skilled in the art.

Figure 28:
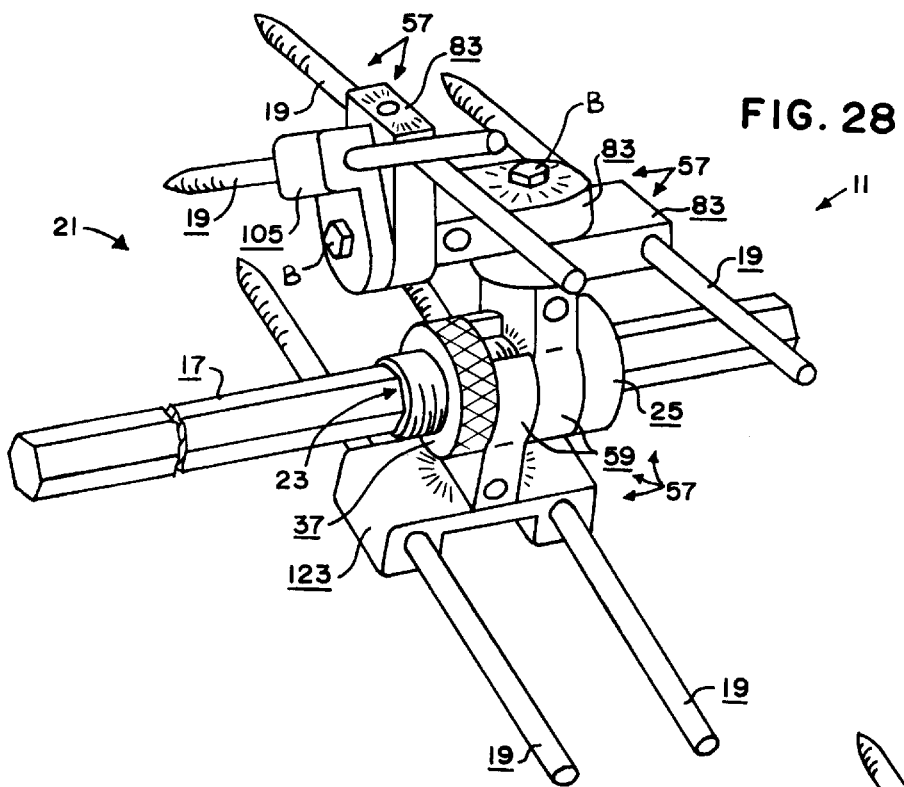
FIG. 28 is a perspective view of a portion of the external fixation system of the present invention, showing a fourth embodiment of the bar-to-pin construct thereof.

FIG. 28 shows a multiple-pin construct in which a single spool 25 is attached to a bar 17, two spool paddles 59 are attached to the spool 25 and stacked side-by-side by being clamped between the flange 29 of the single spool 25 and a locking ring 37, three intermediate paddles 83 are attached to one spool paddle 59 by being stacked side-by-side and side-to-end, a terminal single pin clamp 105 is attached to one of the intermediate paddles 83, a terminal double pin clamp 123 is attached to the other spool paddle 59, and a plurality of pins 19 are attached to the intermediate paddles 83 and pin clamps 105, 123. The coaction between the grip enhancing means 40 on the flange 29 of the spool 25 and the grip enhancing means 75 on one side of the body 63 of one spool paddle 59 and between the grip enhancing means 75 on the adjacent sides of the bodies 63 of the two spool paddles 59 allows accurate and positive angular adjustment of the spool paddles 59 and pins 19 about the longitudinal axis 33 of the bar 17 as will now be apparent to those skilled in the art. Likewise, the coaction between the grip enhancing means 79 on the body 63 of one spool paddle 59 and the grip enhancing means 97 on one side of the body 89 of one intermediate paddle 83, between the grip enhancing means 79 on the body 63 of another spool paddle 59 and the grip enhancing means 137 on one side of the body 129 of the terminal double pin clamp 123, etc., allows accurate and positive angular adjustment of the various components and pins 19 about an axis substantially transverse to the longitudinal axis 33 of the bar 17 as will now be apparent to those skilled in the art. FIG. 28 also illustrates the unique feature of the present invention that allows a threaded attachment or attachment means such as a typical bolt B to pass through an aperture in one or more intermediate components 57 and screw into a threaded aperture in another intermediate component 57 (e.g., through the pin clamp 105 and one intermediate paddle 83 and into another intermediate paddle 83 as shown generally at the upper left of FIG. 28; and/or through two intermediate paddles 83 and into a spool paddle 59 as shown generally at the upper center of FIG. 28). FIG. 28 also illustrates the unique feature of the present invention which allows one of the bolts B to attach a first intermediate component 57 (e.g., one of the intermediate paddles 83) to a second intermediate components 57 (e.g., another of the intermediate paddles 83) with the planar face surface of the two intermediate components 57 engaging one another (as shown generally at the upper center of FIG. 28), and which allows the two intermediate components 57 to be moved away from one another using a shearing motion along the planar face surfaces thereof when the bolt B is removed, thereby allowing adjacent pin attachment nodes to be translated relative to one another without requiring removal of the pins 19, etc., as will now be apparent to those skilled in the art.

Figure 29:
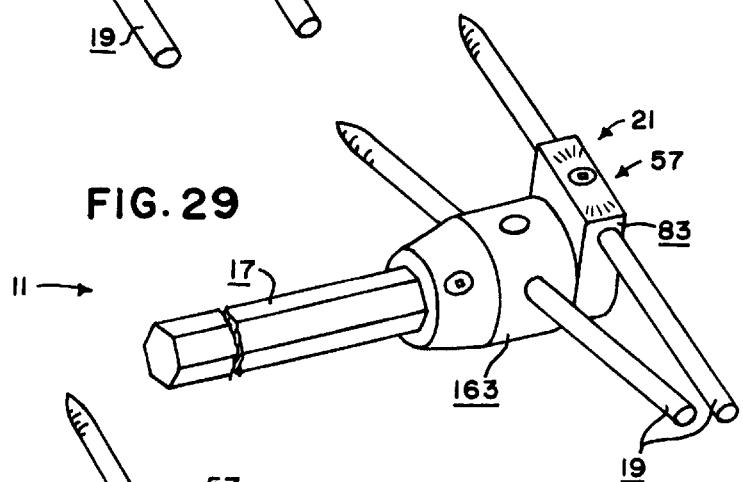
FIG. 29 is a perspective view of a portion of the external fixation system of the present invention, showing a fifth embodiment of the bar-to-pin construct thereof.

FIG. 29 shows a multiple-pin construct in which a single terminal attachment 163 is attached to a bar 17, a single intermediate paddle 83 is attached to the terminal attachment 163, a pin 19 is attached to the terminal attachment 163, and another pin 19 is attached to the intermediate paddle 83. The coaction between the grip enhancing means 179 on the body 165 of the terminal attachment 163 and the grip enhancing means 97 on one side of the body 89 of the intermediate paddle 83 allows accurate and positive angular adjustment of the intermediate paddle 83 and one pin 19 about the longitudinal axis 33 of the bar 17 as will now be apparent to those skilled in the art.

Figure 30:
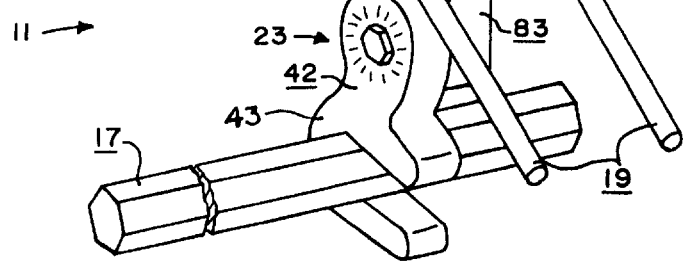
FIG. 30 is a perspective view of a portion of the external fixation system of the present invention, showing a sixth embodiment of the bar-to-pin construct thereof.

FIG. 30 shows a multiple-pin construct in which a single open throat spool 42 is attached to a bar 17, a single intermediate paddle 83 is attached to the open throat spool 42, a double pin clamp 141 is attached to the intermediate paddle 83, and a pair of pins 19 are attached to the double pin clamp 141. The coaction between the grip enhancing means 53 on the ear 49 of the open throat spool 42 and the grip enhancing means 97 on one side of the body 89 of the intermediate paddle 83 allows accurate and positive angular adjustment of the intermediate paddle 83 and one pin 19 about the longitudinal axis 33 of the bar 17 as will now be apparent to those skilled in the art. Likewise, the coaction between the grip enhancing means 79 on the body 63 of one spool paddle 59 and the grip enhancing means 101 on one end of the body 89 of the intermediate paddle 83 and between the grip enhancing means 155 on one side of the body 147 of the double pin clamp 141 allows accurate and positive angular adjustment of the double pin clamp 141 and pins 19 about an axis substantially transverse to the longitudinal axis 33 of the bar 17 as will now be apparent to those skilled in the art. FIG. 30 thus illustrates the unique feature of the present invention that allows a spool component 42 having a one-piece, integral body 43 to be positioned on a bar 17 at locations intermediate the opposite ends of the bar 17, between two previously attached pin-to-pin constructs 11, or the like, as will now be apparent to those skilled in the art.

FIG. 37 shows a multiple-pin construct in which a double spool 183 is attached to a bar 17, an open throat ring adapter spool paddle 197 is attached to the spool 183 on one side of the flange 187 by being clamped between the flange 187 and a locking ring 37, a first "halo" ring 209 is attached to the spool paddle 197 by bolts 211, a pin 19 is attached to the first "halo" ring 209, a spool paddle 59 is attached to the spool 183 on the other side of the flange 187 by being clamped between the flange 187 and a locking ring 37, one intermediate paddle 83 is attached to the spool paddle 59, an intermediate ring adapter 217 is attached to the intermediate paddle 83, a second "halo" ring 209 is attached to the intermediate ring adapter 217 by bolts 231, and a pin 19 is attached to the second "halo" ring 209. The coaction between the grip enhancing means 193 on the flange 187 of the spool 183, the grip enhancing means 213 on one side of the body 201 of the spool paddle 197, and the grip enhancing means 75 on one side of the body 63 of the spool paddles 59, 197 allow accurate and positive angular adjustment of the spool paddles 59, 197 and pins 19 about the longitudinal axis 33 of the bar 17 as will now be apparent to those skilled in the art. Likewise, the coaction between the grip enhancing means 79 on the body 63 of the spool paddle 59 and the grip enhancing means 97 on one side of the body 89 of the intermediate paddle 83, and between the grip enhancing means 101 on the end of the body 89 of the intermediate paddle 83 and the grip enhancing means 225 on one side of the body 221 of the intermediate ring adapter 217 allows accurate and positive angular adjustment of the intermediate paddle 83, intermediate ring adapter 217 and pin 19 about axes substantially transverse and/or spaced from to the longitudinal axis 33 of the bar 17 as will now be apparent to those skilled in the art.

Although the present invention has been described and illustrated with respect to preferred embodiments and preferred uses therefor, it is not to be so limited since modifications and changes can be made therein which are within the full intended scope of the invention.

We claim:

1. A pin-to-bar construct for an external fixation system of the type including a plurality of pins for securing first and second tissue segments, and an elongated bar; said pin-to-bar construct comprising:

(a) a spool for attachment to said bar;

(b) a first component attached to said spool, and including a first aperture therein;

(c) a second component that is directly or indirectly attachable to at least one of said plurality of pins and that includes a second aperture therein; and, (d) a removable fastener that is securely receivable in the first and second apertures;

wherein the spool comprises a cylindrical body and a flange at one end of the body;

wherein the body has a longitudinal aperture extending therethrough for slidably receiving the bar, wherein securing the fastener in the apertures fixedly attaches the first component to the second component;

wherein at least one component is rotatable about the fastener when the fastener is loosened in the apertures whereby the relative positions of the components can be angularly adjusted about the axis of the fastener; and, wherein removal of the fastener from either aperture permits the components to be disconnected from each other without moving the elongated bar relative to the pin.

2. The pin-to-bar construct of claim 1 wherein the longitudinal aperture of the spool includes a first mating surface, and the bar includes a second mating surface, wherein the spool is unable to rotate relative to said bar when positioned on said bar with the first and second mating surfaces adjacent each other.

3. The pin-to-bar construct of claim 1 wherein the spool consists of an open throat spool whereby the spool can be attached to the side of the bar without sliding the spool over either end of the bar.

4. The pin-to-bar construct of claim 1 wherein:
the first component is attached to the cylindrical body of the spool; and
the cylindrical body is long enough to permit additional first components to be attached thereto between the flange and the end of the spool distal the flange;
whereby additional sets of components similar to the first and second components can be attached to the spool.

5. The pin-to-bar construct of claim 4 wherein each first component attached to the spool further comprises a scored surface that mates with a similarly scored surface n any adjacent components attached to the same spool thereby hindering relative motion the adjacent components.

6. The pin-to-bar construct of claim 1 wherein:
the fastener has a headed end and a threaded shank;
the second aperture is larger than the shank but small than the headed end of the fastener; and,
the first component includes threads along the interior surface of the first aperture which mate with the threads on the fastener shank.

7. The pin-to-bar construct of claim 1 wherein the fastener has a headed end and a threaded shank;
the first aperture is larger than the shank but small than the headed end of the fastener; and,
the second component includes threads along the interior surface of the second aperture which mate with the threads on the fastener shank.

8. The pin-to-bar construct of claim 1 wherein the components each have a face surface that surrounds the apertures thereon and a grip enhancing means on the face surface that inhibits movement of the components relative to each other.

9. A pin-to-bar construct for an external fixation system of the type including a plurality of pins for securing first and second fissue segments, and an elongated bar; said pin-to-bar construct comprising:
(a) a spool for attachment to said bar;
(b) a first component attached to said spool, and including a first aperture therein;
(c) a second component that is directly or indirectly attachable to at least one of said plurality of pins and that includes a second aperture therein; and,
(d) a removable fastener that is securely receivable in the first and second apertures;
wherein the fastener has a headed end and a threaded shank;
wherein the second aperture is larger than the shank but small than the headed end of the fastener;
wherein the first component includes threads along the interior surface of the first aperture which mate with the threads on the fastener shank;
wherein securing the fastener in the apertures fixedly attaches the first component to the second component;
wherein at least one component is rotatable about the fastener when the fastener is loosened in the apertures whereby the relative positions of the components can be angularly adjusted about the axis of the fastener; and,
wherein removal of the fastener from either aperture permits the components to be disconnected from each other without moving the elongated bar relative to the pin.

10. A pin-to-bar construct for an external fixation system of the type including a plurality of pins for securing first and second tissue segments, and an elongated bar; said pin-to-bar construct comprising:
(a) a spool for attachment to said bar;
(b) a first component attached to said spool, and including a first aperture therein;
(c) a second component that is directly or indirectly attachable to at least one of said plurality of pins and that includes a second aperture therein; and,
(d) a removable fastener that is securely receivable in the first and second apertures;
wherein the fastener has a headed end and a threaded shank;
wherein the first aperture is larger than the shank but small than the headed end of the fastener;
wherein the second component includes threads along the interior surface of the second aperture which mate with the threads on the fastener shank;
wherein securing the fastener in the apertures fixedly attaches the first component to the second component;
wherein at least one component is rotatable about the fastener when the fastener is loosened in the apertures whereby the relative positions of the components can be angularly adjusted about the axis of the fastener; and,
wherein removal of the fastener from either aperture permits the components to be disconnected from each other without moving the elongated bar relative to the pin.

11. A pin-to-bar construct for an external fixation system of the type including a plurality of pins for securing first and second tissue segments, and an elongated bar; said pin-to-bar construct comprising:
(a) a spool for attachment to said bar;
(b) a first component attached to said spool, and including a first aperture therein;
(c) a second component that is directly or indirectly attachable to at least one of said plurality of pins and that includes a second aperture therein; and,
(d) a removable fastener that is securely receivable in the first and second apertures;
the components each have a face surface that surrounds the apertures thereon and a grip enhancing means on the face surface that inhibits movement of the components relative to each other;
wherein securing the fastener in the apertures fixedly attaches the first component to the second component;
wherein at least one component is rotatable about the fastener when the fastener is loosened in the apertures whereby the relative positions of the components can be angularly adjusted about the axis of the fastener; and,
wherein removal of the fastener from either aperture permits the components to be disconnected from each other without moving the elongated bar relative to the pin.

* * * * *